United States Patent [19]
Bae et al.

[11] Patent Number: 5,262,055
[45] Date of Patent: Nov. 16, 1993

[54] IMPLANTABLE AND REFILLABLE BIOHYBRID ARTIFICIAL PANCREAS

[75] Inventors: You H. Bae; Sun W. Kim, both of Salt Lake City, Utah

[73] Assignee: The University of Utah, Salt Lake City, Utah

[21] Appl. No.: 962,879

[22] Filed: Oct. 19, 1992

[51] Int. Cl.$^5$ ............... B01D 61/00; B01D 63/08; B01D 69/06
[52] U.S. Cl. ................................. 210/645; 210/649; 210/321.75; 210/321.84
[58] Field of Search ............... 210/321.87, 323.1, 634, 210/644–647, 649–654, 321.84, 321.75, 321.71, 321.72; 485/284

[56] References Cited
U.S. PATENT DOCUMENTS
4,578,191 3/1986 Jaffrin et al. ............... 210/321.87

*Primary Examiner*—Frank Sever
*Attorney, Agent, or Firm*—Thorpe, North & Western

[57] ABSTRACT

An artificial pancreas system which minimizes the volume of the artificial pancreas by not encapsulating each islet is taught wherein the islets are separated and held within a polymeric matrix which is soluble in an aqueous solution below body temperature but insoluble in aqueous solutions at or above body temperature. The polymer-islet mixture is contained in a pouch having access means such as entry and exit ports. The solubility makes it possible to replace the contents of the pouch by solubilizing the matrix simply by lowering the temperature below the LCST. The pouch is constructed of a biocompatible material permeable to insulin and other substances of similar or lesser molecular weight but is impermeable to cellular and humoral components of the body immune system. The islet-polymer matrix can be functionalized to stimulate insulin secretion from the islets using insulinotropic agents such as sulfonylurea. Also, polymeric microparticles which release bioactive agents which either promote vascularization at the pouch membrane outer surface or inhibit macrophage activity can be added to the polymer matrix.

29 Claims, 4 Drawing Sheets

IMPLANTABLE AND REFILLABLE BIOHYBRID ARTIFICIAL PANCREAS

This invention relates to a rechargeable islet/polymer matrix system for use in the treatment of Insulin Dependent Diabetes Mellitus. More particularly, this invention relates to a rechargeable system comprising pancreatic islets suspended in a thermosensitive polymer matrix which is water soluble at lower temperatures but solidifies to a gel at body temperature contained within a rechargeable membrane pouch permeable to insulin but impermeable to immunosubstances such as immunoglobulins, antibodies and the like.

BACKGROUND OF THE INVENTION AND STATE OF THE ART

Diabetes Mellitus is one of the most prevalent causes of death by disease in the United States, outranked only by cardiovascular and neoplastic diseases. See Buchwald, *Insulin Replacement: Bionic and Natural*, Trans. Am. Artif. Inter. Organ, 33:675(1984), and *Report of the National Diabetes Advisory Board*, NIH Pub. No. 87-137 (1987). Diabetes is also the leading cause of blindness, kidney related diseases, neurological disorders, cardiovascular diseases, and non-accidental amputation of limbs. See Skylar, *Complication of diabetes mellitus: Relationship to metabolic disfunction*, Diabetes Care, 2:499 (1979); Frier et al., *Does hypoglycemia aggravate the complication of diabetes?* Lancet, 11:1175 (1985); and Pirart, *Diabetes mellitus and its degenerative complications, a prospective study of 4400 patients observed between 1947 and 1973*, Diabetes Metab., 3:173 (1977). Good metabolic control of blood glucose has been the goal of diabetic treatment since the discovery of insulin in 1921 by Banting and Best but has been unobtainable for most diabetic patients. Despite improved treatments using daily insulin injections the majority of insulin dependent patients never maintain the metabolic control necessary for avoiding long-term complications.

Alternative approaches to treat Type I Diabetes Mellitus (to replace daily insulin injections) have been investigated to achieve homeostatic blood glucose levels. The principal concept is to design a biofeedback system in which insulin is released in response to glucose concentrations. At least three approaches thus far have been studied. One is a computer-aided insulin pump with an implanted glucose sensor such as described by Selam et al., *Devices for insulin administration*, Diabetes Care, 13:955 (1990). Another is a glycosylated insulin-bound Concanavalin A system in which glycosylated insulin is released in response to blood glucose levels as described by Brownlee et al., *A glucose-controlled insulin delivery system: Semisynthetic insulin bound to lectin*, Science, 206:1190 (1979); Kim et al., *A self-regulated insulin delivery system*, Edited by T. H. Lee and S. Baba, Excerpta Medica, Amsterdam, (1990), pp. 25-32; and Pai et al., *Concanavalin A microspheres for a self-regulating insulin delivery system*, J. Pharm. Science., (1992), pp. 532-536. Still another approach is the use of immuno-protected islets by an artificial membrane such as reported by Colton et al., *Bioengineering in development of the hybrid artificial pancreas*, J. Biomech. Eng., 113:152 (1991).

Artificial pancreas or other endocrine glands utilizing microencapsulation and/or semi-permeable membranes are disclosed in several U.S. patents of which Sun et al., U.S. Pat. No. 4,323,457; Lim, U.S. Pat. No. 4,391,909 and Loeb, U.S. Pat. No. 4,378,016 are representative. The Sun et al. patent discloses an artificial endocrine pancreas for intravascular implantation and is not rechargeable. The Lim patent teaches microencapsulation of tissue cells such as islet of Langerhans which are injected into the body and purportedly ingested after expiration of the cell life. The Loeb patent is drawn to an implantable artificial endocrine gland consisting of a hollow housing having inserted therein an envelope containing hormone producing cells, e.g. β-cells. The entire envelope is replaced by removal from the housing and there is no consideration of volume of the artificial gland implant and mass transport properties between two separating membranes, i.e. implant housing and envelope membrane.

Although numerous investigations for the above approaches have been reported, only limited successes has been obtained in animal models. See, for example, Lum et al., *Prolonged reversal of diabetic state in NOD Mice by xenografts of microencapsulated rat islets*, Diabetes, 40:1511 (1991); and T. Maki et al., *Successful treatment of diabetes with the biohybrid artificial pancreas in dogs*, Transplantation, 51:43 (1991). Similarly, success in humans has also been restricted. See, for example, Scharp et al., *Insulin independence after islet transplantation into type I diabetic patient*, Diabetes, 39:515 (1990); and Robertson, *Pancreas Transplantation in humans with diabetes mellitus*, Diabetes, 40:1085 (1991).

A most desirable approach in the treatment of Diabetes Mellitus would be through a system utilizing viable islets. The allo- or xenografting of islets, either intravascularly or extravascularly demonstrated the most success in terms of longevity. See Maki et al., supra; Lum et al., supra; and Lacy et al., *Maintenance of normoglycemia in diabetic mice by subcutaneous xenografts of encapsulated islets*, Science, 254:1782 (1991). It was found that extravascular grafting of microencapsulated islets showed a higher success rate in terms of longevity in treating diabetic animals than intravascular transplantation. For the intravascular device, blood contact resulted in thrombosis and fouling of the membrane as reported by Reach, *Bioartificial pancreas: Status and bottlenecks*, Intern. J. Art. Organs, 13:329 (1990). However, while highly desirable, a true implantable artificial pancreas for long-term human application has not yet been developed.

Examples of encapsulation of mammalian cells for biohybrid artificial organs are shown by Galletti, *Bioartificial Organs*, Art. Organs, 16:55 (1992) and Sefton et al., *Microencapsulation of mammalian cells in a water-insoluble polyacrylate by coextrusion and interfacial precipitation*, Biotech. Bioeng. XXIX: 1135 (1987). The development of large-scale cell culture for cell products is taught by Chang, *Artificial cells: 35 years*, Art. Organs, 16:8 (1992). The information obtained from these investigations stress that the encapsulation material should be nontoxic to the cells and requires different degree of mechanical strength, permeability, and biocompatibility, depending on the cells to be encapsulated and their applications. Historically, alginate-poly(L-Lysine)-alginate complexes have been used as encapsulating materials, especially for a biohybrid artificial pancreas. This system is based on the ionic interaction of polyanion (alginate) and polycation [poly(L-lysine)] to complex around the islets, forming an immuno-protective boundary, and still permitting diffusion of glucose and insulin as shown by Goosen et al., *Optimization of microencapsulation parameters: Semipermeable microcapsules as a*

*bioartificial pancreas*, Biotech. Bioeng., XXVII:146 (1985).

The treatment of diabetes with peritoneal implants of encapsulated islets in in vivo diabetic models has been reported by several research groups. See, for example, Colton et al., supra; Reach, supra, and Warnock et al., *Critical mass of purified islets that induce normoglycemia after implantation into dogs*, Diabetes, 37:467 (1988). Their accumulated data from human and animal experiments have determined that the number of islets required to reverse diabetes is up to 5,000 islets/kg. This figure suggests that a 70 kg patient will need ≈350,000 islets to maintain suitable blood glucose levels. The volume of encapsulated islets (assuming that a mean capsule diameter containing one islet is ≈500 μm) would be ≈18 mL, and have a surface area of ≈2750 cm$^2$. Therefore, to be clinically applicable, it would be necessary to reduce the volume and surface area of a biohybrid artificial pancreas.

A major consideration for the design of a biohybrid artificial pancreas is to prolong cell survival within the system. In general, peritoneally implanted membrane encapsulated cells have a limited life span. This is probably due to oxygen deficiency and inactivation of the cells by low molecular weight humoral components of the immune system, such as interleukin-1, although the membrane will isolate the entrapped islets from the cellular immune system or high molecular weight cytokines. Once cell lysis occurs, foreign proteins released from the cells will accelerate the attack of cellular immune system. From this perspective, it is essential that the implanted islets in any form (intra- or extravascular graft, entrapped in housing, hollow fiber, or capsule) should be retrievable or replaceable with fresh islets after a certain period of time. Thus far, the approach to islet implantation (free floating encapsulated cells) in the peritoneal cavity has been limited in practical human application in terms of recovery or replacement of cells. It would therefore be desirable to design a self-contained miniaturized implant from which the islets can be replenished after a certain period of time. Such an approach may also allow sampling of the device for evaluating its status during treatment, without operating on or sacrificing the animal. Another advantage of a self-contained device would be the easy retrieval of islets during an emergency.

OBJECTS AND BRIEF SUMMARY OF THE INVENTION

It is an object of the present invention to provide a rechargeable extravascularly implantable biohybrid artificial pancreas.

It is also an object of this invention to provide a biohybrid artificial pancreas comprising an implantable refillable immunoprotective membrane pouch containing an islet-polymer matrix wherein the polymer is soluble below body temperatures and insoluble at or above body temperature.

A still further object of the invention is to provide an artificial pancreas having an implantable refillable pouch containing an islet-polymer matrix wherein the pouch contains means for stimulating the insulin secretion function of β-cells of the islets.

Yet another object of this invention is to provide an artificial pancreas which releases bioactive agents which regulate interactions between the artificial pancreas membrane and cellular components in the body and wherein the membrane isolates the islets from cellular and humoral components in the body immune system.

These and other objects may be accomplished by a system which minimizes the volume of the artificial pancreas by not encapsulating each islet as in the past. Rather, the islet cells are separated and held within a polymeric matrix which is soluble in an aqueous solution below body temperature but insoluble in aqueous solutions at or above body temperature, i.e. about 37° C. The polymer-islet mixture is contained in a pouch having entry and exit ports. The solubility makes it possible to replace the contents of the pouch by solubilizing the matrix simply by lowering the temperature, e.g. by injecting cold saline into the pouch, placing a cold pack adjacent the pouch, or by any other suitable means which produces localized hypothermia. The pouch is constructed of a biocompatible material permeable to insulin and other substances of similar or lesser molecular weight, including oxygen, nutrients and other body hormones which may pass in either direction into or out of the pouch. However, the pouch is impermeable to cellular and humoral components of the body immune system. Additionally, the islet-polymer matrix can be functionalized to stimulate insulin secretion from the islets. For example, insulinotropic agents such as sulfonylurea, can be grafted onto the thermosensitive polymer matrix to increase the efficiency of the system. Because sulfonylurea is a cell-surface active agent, it does not have to be internalized into the islet cells to promote insulin secretion. Therefore, sulfonyl urea, covalently coupled to the polymer chain, will interact with the entrapped islets to enhance insulin release. The degree to which insulinotropic agents amplifies the secretion of insulin may allow a corresponding reduction in the pouch volume of the artificial pancreas.

By use of the term "pouch" or "pouch membrane" is meant any biocompatible structure which performs the function of holding the islet/thermosensitive polymer suspension, has the appropriate molecular cutoff, and has access means for recharging the pouch interior with fresh amount of islet/thermopolymer in liquid form. Such structure may be in the form of a hollow fiber, tube, bag or the like and still be referred to as a "pouch" for purposes of the present invention.

Therefore, in summary, the present invention is drawn to an artificial pancreas device comprising a pouch membrane of superior design and function requiring minimal space while affording optimal implant volume. The implant, consisting of islets suspended in Lower Critical Sensitive Temperature polymers having a LCST which are liquid at low temperatures, form solid microsphere/cell matrix particles at body temperature, can be sampled and/or replaced as desired. The suspension may also contain islet stimulating agents and/or other particles which release bioactive agents.

DESCRIPTION OF THE PREFERRED EMBODIMENTS

Since there is no practical method available to isolate sufficient islets from a single human donor for a human recipient it will be necessary to efficiently harvest and store islets isolated from mammalian pancreases for transplantation. Recently, several research groups investigated cryopreservation as a method to store and preserve islets. See, for example, Hullett et al., *Successful long-term cryopreservation and transplantation of human fetal pancreas*, Diabetes, 38:448 (1989); and Kneteman et al., *Long-term cryogenic storage of purified adult human islets of Langerhans*, Diabetes, 38:386 (1989). These cells maintained biological activity and are considered to be suitable for grafting into diabetic animal models. Thus, islets from animal sources can be frozen for long-term storage and are suitable for utilization in the hybrid artificial pancreas of the present invention.

Figure 1:
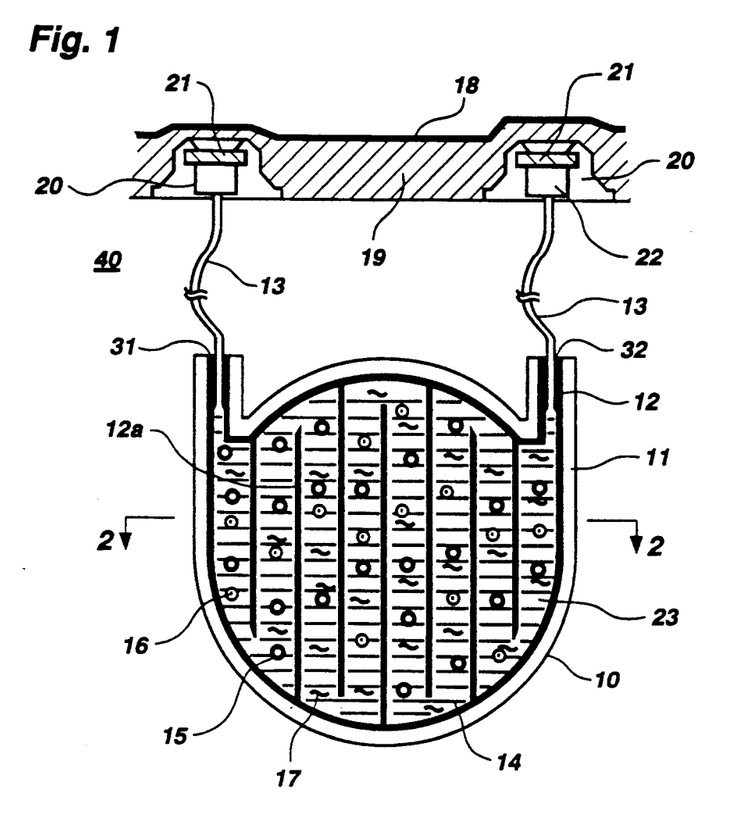
FIG. 1 is a cross sectional view of a rechargeable artificial pancreas system implanted in a patient.

There is shown in FIG. 1 a complete embodiment of the invention consisting of an implantable pouch 10, which can be used for the treatment of Insulin Dependent Diabetes Mellitus using replaceable polymer-islet formulation. The pouch 10 is formed from parallel membrane walls 11 sealed in a fluid tight relationship around the perimeter along line 12 and also along generally parallel lines 12a intermittently extending from the bottom or top of said pouch structure to form an interior reservoir 23 having a continuous but winding flowpath. The pouch contains an inlet port 31 accessing the inlet to said reservoir flowpath and an outlet port 32 leading from said reservoir flowpath said inlet and outlet ports being connected via tubing 13 subcutaneous access devices 20 consisting of a needle receptacle 22 covered by a septum 21. The pouch as defined is relatively flat as defined by membrane walls 11 however the perimeter defined by seal line 12 can be circular or of any other desired shape as long as fluid, i.e. liquid thermosensitive polymer or cold saline or other solution, can be moved through said reservoir 23 along said reservoir flowpath from said inlet port 31 and out through said outlet port 32.

The pouch reservoir 23 contains a thermosensitive polymeric matrix 14 having entrapped or suspended therein islets 15 and, optionally, one or more particles 16, for releasing bioactive agents inhibiting macrophage or promoting vascularization. In addition, the polymer may contain or have grafted thereto islet stimulating substances 17. In the alternative, separate and apart from the thermosensitive polymers in which the islets are suspended, islet stimulating substance grafted water-soluble polymers or proteins can be entrapped in the pouch.

As illustrated in FIG. 1 the pouch is inserted extravascularly, such as in the peritoneal cavity 40, and is secured so that the access device 20 is positioned subcutaneously in the fat tissue layer 19 below the skin 18.

The functionality of the present invention is made possible by the physical characteristics of the thermosensitive polymer. Some of the advantages attributable to the use of a thermosensitive polymeric matrix lie in the discovery that such use can (1) reduce the implant volume by not encapsulating each islet, (2) physically separate islet within a polymeric pouch, (3) use an aqueous solvent rather than an organic solvent to prepare the polymer-islet system, and (4) make it possible to replace the contents of the pouch by solubilizing the matrix by lowering temperature.

The phenomenon of thermally reversible precipitation of aqueous polymer solutions or swelling transition of the corresponding crosslinked gel is documented by Marchetti et al., *Thermodynamic predictions of volume changes in temperature-sensitive gels*. 1. Theory, Macromol., 23:1760 (1990). Swelling transitions in an aqueous system are based on the lower critical solution temperature (LCST), at which the soluble polymer molecules undergo transition from a random coil to a globular state, becoming insoluble when the temperature is raised above the LCST. This phenomenon is attributed to entropically driven dehydration of the polymer. This means the major interactions in the system switches from hydrogen bonding to hydrophobic interaction at the LCST. See Bae et al., *Temperature dependence of swelling of crosslinked poly(N,N-alkyl substituted acrylamide) in water*, J. Polym. Sci.: Part B: Polym. Phys., 28:923 (1990). Thus, the LCST behavior is typically found in aqueous solutions of hydrophilic/hydrophobic balanced water soluble polymers, and is affected by the chemical structure of the repeat unit and comonomers used in the synthesis. See Bae et al., supra, and also Taylor et al., *Preparation of films exhibiting a balance temperature dependence to permeation by aqueous solution-A study of lower consolute behavior*, J. Polym. Sci.: Polym. Chem. Ed., 13:2551 (1975).

Among synthetic polymers exhibiting temperature induced transitions, poly(N-isopropylacrylamide) or "poly(NiPAAm)" and related copolymers were investigated for pharmaceutical applications. In cell culture applications, poly(NiPAAm) was coated or grafted on polystyrene petri dishes. Cells such as fibroblast and hepatocyte were cultured on the coated dishes at 37° C. as shown by Takezawa et al., *Cell culture on a thermoresponsive polymer surface*, Bio/Technology, 8:854 (1990) and Yamada et al., *Thermoresponsive polymeric surface; control of attachment and detachment of cultured cells*, Makromol. Chem., Rapid Commun., 11:571 (1990). Harvesting of the cells was accomplished by decreasing the temperature, rather than using trypsin or collagenase digestion. At low temperature, the grafted polymer expands and repels the cultured cell with nearly a 100% yield of intact cells. This attests to the fact that the poly(NiPAAm) polymer is nontoxic and has adhesive propeties to cells in a collapsed state at body temperature. In addition, the thermal transition or mass transport properties of this synthetic polymer to solutes can be modified by incorporating more hydrophilic or hydrophobic comonomers or charged groups into the polymer as shown by Hoffman et al, *Thermally reversible hydrogels. II Dilivery and selective removal of substances from aqueous solution*, J. Control. Rel., 4:213 (1986); Bae et al., *Thermo-sensitive polymers as on-off switch for drug release*, Makromol. Chem., Rapid Commun., 8:481 (1987) and Beltran et al., *Swelling equilibria for weakly ionizable, temperature-sensitive hydrogels*, Macromol., 24:549 (1991).

From the above discussion it is evident that two of the more critical aspects of the present invention are in the pouch membrane and in the thermally sensitive polymer. The pouch membrane 11 can be made of any tissue compatible, immuno-protective semi-porous membrane material having a molecular cutoff size of between about 10,000 and 100,000 daltons and preferably between about 20,000 to 60,000 daltons. The membrane can be a single layer film, a composite, a coated layer or a laminated material.

Cellulose derivatives are particularly useful for molecular cutoff purposes. For example, one may choose an appropriate cellulose material selected from the group consisting of cellulose, cellulose hydrate, cellulose acetate, cellulose esters, cellulose ethers, cellulose ester-ethers, cellulose acrylate, cellulose diacrylate, cellulose triacrylate, hydroxypropyl methyl cellulose and mixtures of any of the above.

One may also use synthetic membranes for molecular cutoff purposes or as porous supporting membranes. Exemplary are membranes selected from the group consisting of poly(acrylonitrile-co-vinyl chloride), polysulfone, poly(vinylidene fluoride), ethylene vinylacetate, polyethylene, polypropylene, polycarbonate and polytetrafluoroethylene.

A particularly preferred membrane is a top coated porous heat sealable membrane. Such a membrane may be made of poly(vinylidene fluoride), ethylene vinylacetate, poly(acrylonitronitrile-co-vinyl chloride) or polypropylene having a membrane porosity of about 10–95% and preferably of 60–90% and be covered with a thin top coating made of cellulose or cellulose acetate possessing the desired molecular cutoff and biocompatibility. Such a top coating may be accomplished by means of spin coating, solvent casting, or other suitable technology to produce the desired membrane.

The thermosensitive polymer matrix is one having a liquid-solid transition temperature (lower critical solution temperature "LCST") of between about 0° and 40° C. and preferably between about 15° and 35° C.

Thermosensitive polymers are made up of monomers or mixtures of such monomers polymerizable by free radical or ionic initiation which results in polymers having LCST in aqueous systems as stated above. Suitable are the N-alkyl or N,N-dialkyl substituted acrylamides or methacrylamides of the formula:

where R is hydrogen or methyl, $R^1$ is a member selected from the group consisting of lower alkyl and lower alkoxyalkyl and $R^2$ is a member selected from the group consisting of hydrogen, lower alkyl and lower alkoxyalkyl with the proviso that $R^1$ and $R^2$ can combine as an alkylene —$(CH_2)_n$— chain to form a N-cyclic structure where n is an integer of 4 to 6. n is preferably 5. By lower alkyl or alkoxy is meant a straight or branched carbon chain containing from one to eight carbon atoms and preferably from one to five carbon atoms. Mixtures of one or more of the above monomers may also be utilized as temperature sensitive components.

Exemplary of such temperature sensitive monomers are those selected from the group consisting of N-isopropylacrylamide ["NiPAAm"], N,N-diethylacrylamide, N-acryloylpiperidine, N-methylmethacrylamide, N-ethylmethacrylamide, N-n-propylacrylamide and N-(3'-methoxypropyl)acrylamide. The preferred temperature sensitive monomers are the lower alkyl acrylamides which are selected from the group consisting of N-isopropylacrylamide, N,N-diethylacrylamide and N-n-propylacrylamide.

As previously stated, the thermal transition properties of thermosensitive polymers can be modified by incorporating more hydrophilic or hydrophobic comonomers or charged groups into the polymer. Hydrophobic monomer units tend to lower the LCST while hydrophilic or charged groups tend to raise the LCST. Some charged monomers may also be pH sensitive and the change in pH may also affect the LCST.

Suitable hydrophobic monomer components which can be incorporated into the thermosensitive polymers to lower the LCST include any water insoluble monomers which are copolymerizable with the thermosensitive monomer components. Suitable monomers have the formula:

wherein $B^1$ and $B^2$ are members selected from the group consisting of hydrogen, halo, aryl, alkenyl and alkyl. $D^1$ is a member selected from the group consisting of hydrogen, lower alkyl, lower alkenyl and halo and $D^2$ is a member selected from the group consisting of a lower alkyl carboxylate, aryl, cyano and N-carbazole. $D^2$ can also be any other similar functional grouping which imparts the desired physical hydrophobic characteristics and is copolymerizable with the other components. Preferably $B^1$ and $B^2$ will be hydrogen, $D^1$ is either hydrogen or lower alkyl, methyl in particular, and $D^2$ is a member selected from the group consisting of a lower alkyl carboxylate, phenyl and cyano.

Exemplary of such monomers are lower alkyl acrylates or methacrylates, 1,3-diene monomers, α-methyl styrene, halogenated olefins, vinyl esters, acrylonitrile, methacrylonitrile, N-vinyl carbazole and the like. Preferred are alkyl acrylates and methacrylates having the following formula:

$$CH_2=CR''—COOR^3$$

wherein R'' is hydrogen or methyl and $R^3$ is a lower alkyl having from 1 to 8 carbon atoms and styrene, α-methyl styrene, acrylonitrile and methacrylonitrile. Particularly preferred are the lower alkyl esters of acrylic acid and methacrylic acid such as methyl, ethyl, propyl, isopropyl, butyl and amyl acrylate and methacrylate and styrene.

The hydrophobic component comprises between about 0.5 to 30% by weight and preferably between about 1 to 20% by weight of the thermosensitive polymer.

Charged or hydrophilic monomer units which may be pH sensitive as well as raise the LCST of the thermosensitive polymers may also be incorporated into the polymer chain. Suitable charged or hydrophilic monomer units may be selected from the group consisting of N,N-dimethylaminoethylacrylate, N,N-diethylaminoethylacrylate, N,N-dimethylaminopropylacrylate, N,N-diethylaminopropylacrylate, N,N-dimethylaminoethylmethacrylate, N,N-diethylaminoethylmethacrylate, N,N-dimethylaminopropylmethacrylate, N,N-diethylaminopropylmethacrylate, N,N-dimethylaminoethylacrylamide, N,N-diethylaminoethylacrylamide, N,N-dimethylaminopropylacrylamide, N,N-diethylaminopropylacrylamide, N,N-dimethylaminoethylmethacrylamide, N,N-diethylaminoethylmethacrylamide, N,N-dimethylaminopropylmethacrylamide, N,N-diethylaminopropylmethacrylamide, acrylic acid, methacrylic acid, N-vinyl pyrrolidone, acrylamide, methacrylamide, N-methylacrylamide, N,N-dimethylacrylamide, N-ethylacylamide, 2-hydroxy ethyl methacrylate, hydroxy propylmethacrylate, methoxyethoxyethyl methacrylate and methoxyethyl methacrylate.

In addition to the above, any polymers made from hydrophilic/hydrophobic monomer combinations to give the desired LCST or any cellulose derivatives which have the desired LCST and any hydrophilic/hydrophobic block or graft copolymers which have a desired LCST or sol-gel transition temperature may be utilized without departing from the scope of the invention. The limitation of suitable thermosensitive polymers does not lie in any particular chemical structure. Rather, it is the functionality of the polymer in having the desired LCST properties that controls its utility.

Another embodiment of this invention resides in the ability to functionalize the thermosensitive polymer matrix to stimulate insulin secretion from the islets. For example, insulinotropic agents, such as sulfonylurea, can be grafted into the thermosensitive polymer matrix or into other water-soluble polymers or proteins to increase the efficiency of the system. While sulfonylurea is specifically exemplified, the invention is not to be limited to any specific chemical which stimulates insulin secretion. Any chemical or chemicals which stimulate insulin secretion from islets or enhance the stimulatory effects of glucose and other insulin secretagogues on insulin secretions are also included. Sulfonylurea, or any other insulin stimulating chemicals, grafted onto the thermosensitive LCST polymers or other water soluble polymers or macromolecules are included within the scope of this invention.

Sulfonylurea derivatives are currently used to treat non-insulin dependent Type II Diabetes. Their ability to stimulate insulin secretion and to enhance the stimulatory effects of glucose and other insulin secretagogues on insulin secretions are documented by Loubatieres et al., *Studies on insulin secretion in the perfused rat pancreas: Synergistic effect of glucose and hypoglycemic sulfonamides*, Diabetologia, 6:457 (1970); Malaisse et al., *The stimulus secretion coupling of glucose-induced insulin release. VIII. Combined effects of glucose and sulfonylureas*, Eur. J. Clin. Invest., 2:85 (1972); and Group et al., *Dose-dependent effects of glyburide on insulin secretion and glucose uptake in humans*, Diabetic Care, 14:724 (1991). Mechanistically, as reported by Boyd III, *Sulfonylurea receptors, ion channels, and fruit flies*, Diabetes, 37:847 (1988); and Misler et al., *Metabolite-regulated ATP-sensitive $K^+$ channel in human pancreatic islet cells*, Diabetes, 38:422 (1989) sulfonylureas react with a cell surface APT-sensitive $K+$ channels causing membrane depolarization in an influx of $Ca^{2+}$ through voltage sensitive $Ca^{2+}$ channels. The rise in the intracellular free $Ca^{2+}$ levels then triggers the exocytosis of insulin.

Since the sulfonylurea molecule is most likely a cell-surface active drug, it does not have to be internalized into the islets to promote to insulin secretion. Therefore, sulfonylurea covalently coupled to the thermosensitive polymer chain will interact with the entrapped islets to enhance insulin release. If a certain degree of the amplification of insulin secretion is obtained, there will be an increasing ability to reduce implant volume. This concept can also be expanded to other functional polymers which are able to regulate cell functions, such as cell growth, proliferation and secretion.

Figure 5:
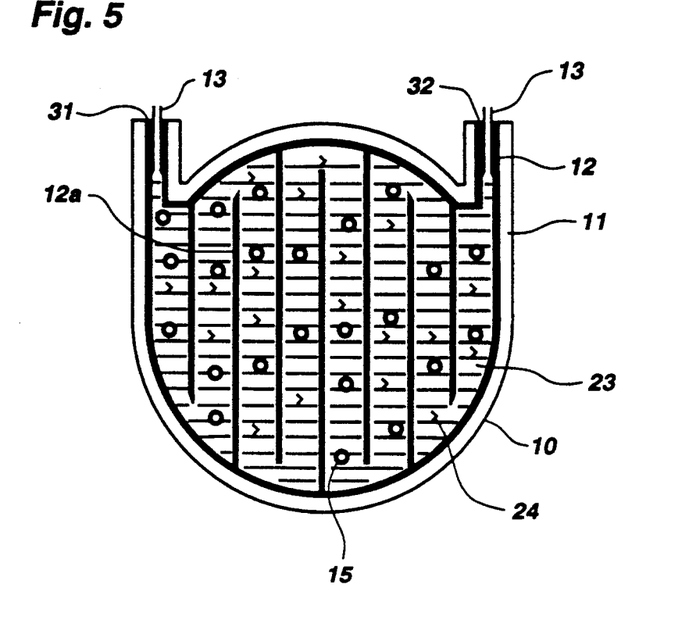
FIG. 5 shows an embodiment as illustrated in FIG. 1 without the presence of particles which release bioactive agents.

Therefore, thermosensitive polymers grafted with islet stimulants, such as sulfonylurea and its derivatives, form an embodiment of the invention which is illustrated in FIG. 5 as will be discussed.

Additionally, the thermosensitive polymer matrix may contain microparticles which release bioactive agents which either promote vascularization at the pouch outer surface or inhibit macrophage activity. Polymeric microparticles ranging in size of between about 0.1 $\mu$m to 1000 $\mu$m and preferably between about 200 $\mu$m to 500 $\mu$m, such as ethylene vinylacetate, polyactide, polyglycolide, poly(lactide/glycolide), polymethacrylic acid, albumin and alginate and the like. These particles can contain and release bioactive agents i.e. nicotinamide; anti-inflammatory agents such as dexamethasone, indomethacin and ketoprophen; immunosupressants such as corticosteriods, cyclosporine, cyclophosphamide, adrenocorticosteroids, FK-506, methoxsalen and thalidomide; and angiogenic factors such as acidic fibroblast growth factor, basic fibroblast growth factor, angiogenin, transforming growth factor $\alpha$, transforming growth factor $\beta$ and heparin-binding growth factor-I.

The tubing 13 connecting pouch 10 with the access device 20 may be made of any suitable inert flexible material such as polyethylene, polypropylene, silicone, polyurethane, plasticized polyvinyl chloride and the like.

Figure 7:
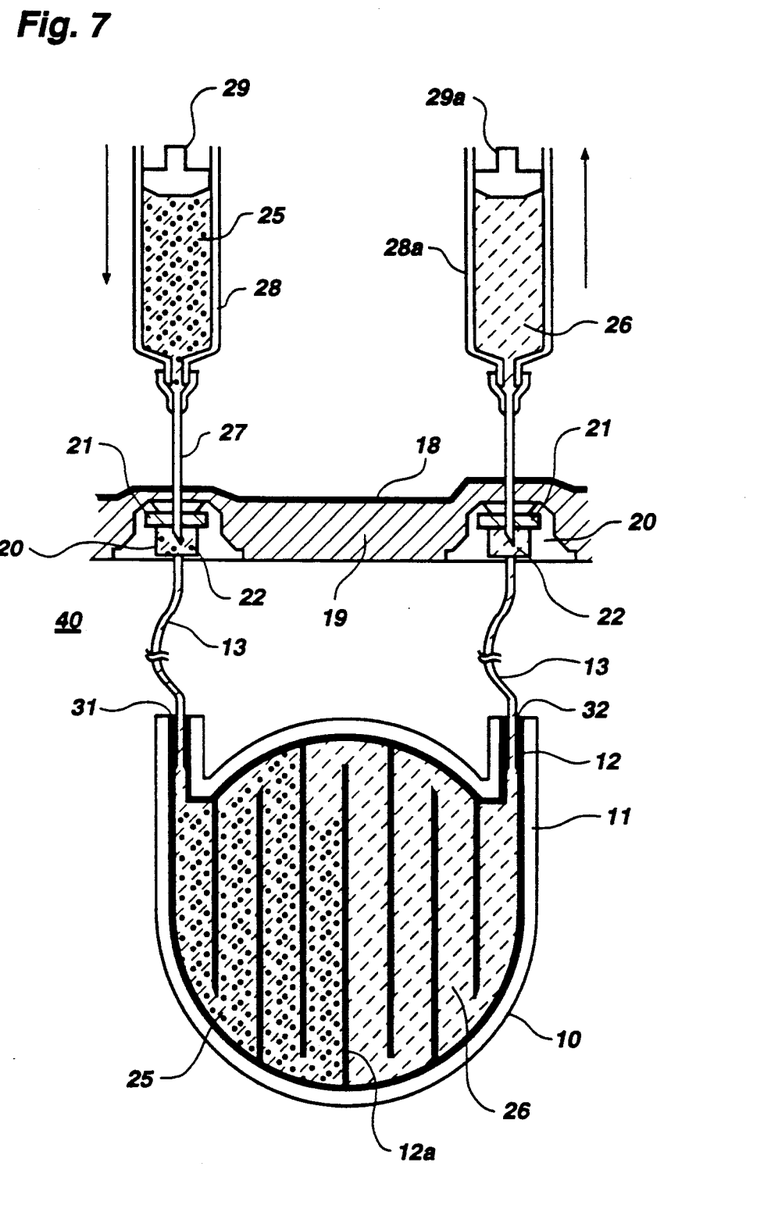
FIG. 7 is a cross sectional view of the system shown in FIG. 1 further illustrating the process for filling or replacing the pouch contents under hypothermic conditions.

The islets 15, and any other particles, bioactive agents, or additives 16, and polymers grafted with insulin stimulating molecules 17, will be suspended in the selected thermosensitive polymer or copolymer at a temperature below the LCST as a liquid suspension. This suspension will be injected into the designed pouch 10 and the polymer 14 will collapse surrounding and protecting the islets 15 and other particles 16 and 17 (as hereinafter described) as the temperature is raised to or above the LCST. Decreasing the temperature within the pouch (by inducing localized hypothermia such as by application of ice packs placed next to the pouch or by injecting cold saline or any other suitable solution into the pouch) will solubilize the collapsed matrix for easy removal. This procedure is illustrated in FIG. 7. Cold saline solution 25 in a syringe 28 is pushed by piston 29 through needle 27 inserted into septum 21 and needle insertion space 22 through tubing 13 into the inlet port 31 of pouch reservoir 23. The cold saline 25 entering reservoir 23 lowers the temperature of the existing polymer matrix 26 below the LCST causing it to liquify. A companion syringe 28a, having piston 29a is pulled upward drawing liquified polymer solution 26 up through outlet port 32 via tubing 13 into a needle 27a inserted into needle insertion space 22 through septum 21 and into the barrel of the syringe 28a. When the pouch reservoir 23 is filled with cold saline as indicated by the presence of saline in the barrel of syringe 28a the reservoir can be filled with fresh polymeric solution by repeating the procedure using cold polymer solution in syringe 28. In the alternative, instead of using cold saline, cold fresh polymer solution could be used to lower the temperature of the expended polymer and liquify it for removal. By using a pouch of known volume the exchange of polymer in solution form can be measured and a recharge volume can be readily determined. It is apparent that there are various ways of producing localized hypothermia in the pouch area and recharging the polymer reservoir without having to remove the pouch surgically which is a definite advantage not heretofore found in any prior art device for an artificial endocrine gland.

Various embodiments of the invention containing a polymeric matrix 14 and entrapped islets 15 are illustrated in FIGS. 1 through 6 and will now be described in detail.

Figure 2:
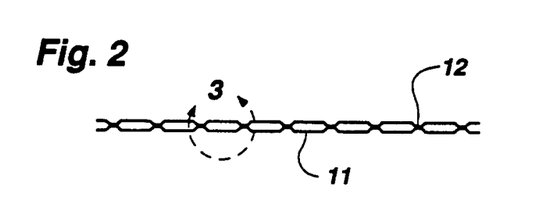
FIG. 2 is a cross sectional view of the pouch portion of the artificial pancreas taken along plane 2—2 of FIG. 1.
Figure 3:
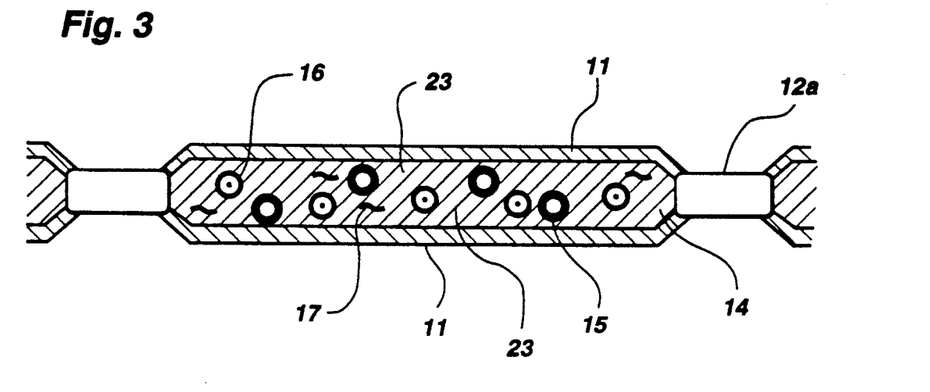
FIG. 3 is an enlargement of the segment shown in dotted lines of FIG. 2 showing islets and other particles suspended in a thermosensitive polymer matrix.

FIGS. 1-3 show an embodiment wherein pouch 10 is filled with a polymer matrix 14 having suspended or entrapped therein islet 15, particles releasing bioactive agents which inhibit macrophage or promote vascularization 16 and polymers having insulin stimulating molecules (e.g. sulfonylurea) grafted thereon.

Pouch 10 is fabricated by sealing together two membranes 11 by means such as heating with pressure, glue or any other means to form a pouch 10 having a reservoir 23. The pouch is sealed along the perimeter and also may be sealed along alternating lines which partially extend from top to bottom of the pouch parallel to each other across the pouch diameter to function as spacers and create uniform flow path. Obviously, the sealing across the pouch could be by non parallel lines or any other means as long as the pouch membranes are held in close relationship so as not to expand or balloon and also provide a continuous pathway allowing uniform flow into and out of the pouch when the contents are replaced. The pouch is sized to hold a volume of islets (e.g. $\approx$ 5000/kg body weight) entrapped in a thermosensitive polymer matrix sufficient to treat a diabetic condition. The pouch may be of any suitable dimensions and geometry. The pouch shown in the drawings is illustrative only of one embodiment of a suitable subcutaneous peritoneal access device (SPAD). The SPAD may have a separate inlet and outlet as shown in the figures or may have a single access opening used for both filling and removal of the pouch reservoir implant. Therefore, any pouch design having a reservoir for holding the LCST polymer/cell suspension and which functions in the manner described herein is suitable regardless of specific geometry or design, geometry or dimensions.

As previously stated, the term "pouch" or "pouch membrane" is meant to encompass any biocompatible structure which performs the function of holding the islet/thermosensitive polymer suspension providing it has the appropriate molecular cutoff and has access means for recharging the pouch interior with fresh amount of islet/thermosensitive polymer in liquid form. Any such structure having an interior reservoir may be used regardless of name or specific form, i.e. packets, hollow fibers, tubes, bags, sacks, purses, pouches or the like are collectively referred to as a "pouch" for purposes of the present invention. Preferably, the design and geometry will be that which will allow the minimal pouch volume to produce the maximum results relative to insulin release. A flat pouch as illustrated in the figures may have a side diameter of between about 2 to 15 cm with a diameter of between about 4 to 7 cm being preferable. As shown in the examples which follow, a flat pouch having a diameter of 4 cm, with five intermittent sealings of 1 mm producing a winding reservoir pathway of about 6 mm in width would have a volume of about 1 ml.

The islets are isolated from each other by being suspended in the polymer matrix and therefore do not aggregate. This minimizes resistance to mass transport of the insulin secreted by the cells. The pouch 10 is accessed via inlet and outlet ports 31 and 32 respectively connected via tubing 13 to a subcutaneous peritoneal access device 20 consisting of a space for needle insertion 22 covered by a septum 21.

FIG. 2 illustrates the device in top cross section taken along the plane 2—2 of FIG. 1. As can be seen, the pouch is thin allowing for the membranes 11 to have a suitably large membrane surface area. FIG. 3 is an enlargement of the dotted box of FIG. 2 showing the suspension of entrapment of islets 15, bioactive particles 16 and insulin stimulating molecules grafted to polymers 17 suspended in the polymer matrix 14. The walls of membrane 11 are sufficiently porous that insulin and bioactive materials released from the matrix 14 can pass through the membrane walls and into the surrounding environment where, in the case of insulin, it is picked up or transported via the circulation system and, in the case of other bioactive agents, either promotes the vascularization of the pouch or inhibits macrophage. The insulin stimulating molecules interact with the islets to promote the production and release of insulin and therefore allow for a smaller pouch volume than might otherwise be necessary. The membrane walls have a molecular cutoff that prohibits bacteria, lymphocytes, and large proteins from entering into the pouch and inhibiting proper metabolic functioning of the cells while, at the same time, allowing nutrients, ions, oxygen and other materials to enter into the pouch. When it is determined that the in vivo life of the islets is drawing to an end, the entire polymeric matrix can easily be replaced in the manner indicated above by lowering the temperature of the polymeric matrix below the LCST, by any suitable means, and replacing the liquid polymer solution with fresh polymer solution containing islets and such other ingredients as desired.

Figure 4:
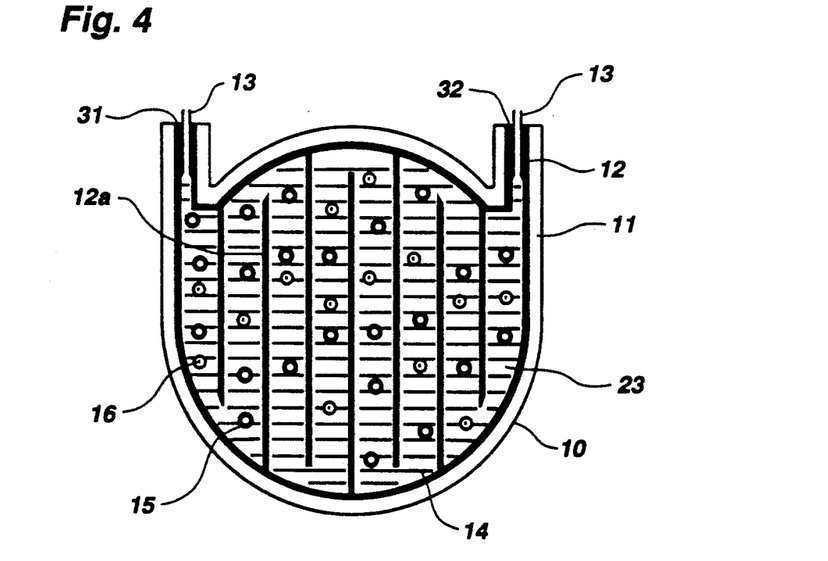
FIG. 4 shows an embodiment as illustrated in FIG. 1 without the presence of islet stimulants.

FIG. 4 shows an embodiment which differs from FIGS. 1-3 only in that the polymeric matrix 14 contains only entrapped islets 15 and particles containing bioactive agents 16. In other words, the insulin stimulating molecules grafted to the thermosensitive polymer network are not present.

FIG. 5 differs from FIGS. 1-3 in that the polymeric matrix 14 contains entrapped islets 15 and insulin stimulating molecules 16 and does not contain particles containing other bioactive agents.

Figure 6:
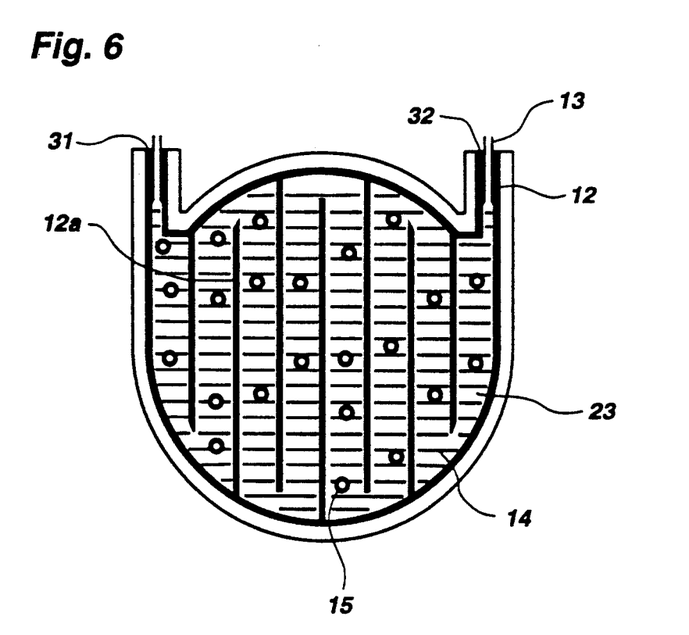
FIG. 6 shows an embodiment as illustrated in FIG. 1 without either islet stimulants or particles which release bioactive agents.

FIG. 6, illustrates the simplest embodiment of the invention showing only the presence of islets 15 entrapped in the polymeric matrix 14 contained in reservoir 23.

Obviously, any combination of the embodiments illustrated may be utilized. A polymeric matrix containing only islets may be replaced by a matrix containing insulin stimulating molecules, etc. This allows the practitioner to vary the treatment according to the needs of the patient.

The following examples are illustrative of a preferred embodiment of the invention.

EXAMPLE 1

Preparation of an LCST Polymer

N-isopropylacrylamide (NiPAAm) was polymerized using tert-butyl peroxyoctanoate (BPO) as an initiator. NiPAAm (3 g) was dissolved in 3 ml of distilled 1,4-dioxane, followed by the addition of 9 μl of BPO. The solution was bubbled with dried nitrogen gas for 20 minutes. The solution was then polymerized at 80° C. in a constant temperature oven for 12 hours. The resulting polymer was precipitated in an excess amount of hexane, filtered and dries. The lower critical solution temperature (LCST) of the polymer was about 32° C.

EXAMPLE 2

Grafting of Sulfonylurea onto Polymers

Sulfonylurea was coupled to vinyl monomers through covalent bonding and copolymerized with NiPAAm. Methacryloyl chloride (0.105 mole), cooled to 10° C., was added to a solution [130 ml of water/acetone mixture (1/1 v/v) containing 0.1 mole of NaOH and 0.1 mole of N-4-(aminobenzylsulfonyl)-N-butylurea] (a sulfonylurea: carbutamide) under stirring. The precipitate was filtered, washed with distilled water, dried in vacuum and recrystallized from acetonitrile. This monomer, containing a sulfonyl urea substituent, was copolymerized with NiPAAm using the method as in Example 1. The content of the monomer having sulfonyl urea substituents in the copolymer was about 10%.

EXAMPLE 3

Preparation of a Pouch Membrane

Cellulose acetate (39% acetyl content) powder was dissolved in glacial acetic acid (9 w/v %) and filtered through a 0.45 μm filter membrane. The substrate membrane, Durapore ® [poly(vinylidene fluoride), 0.1 μm pore size, 80% porosity] was mounted on a spin coater plate by applying vacuum from beneath the spinning chuck. The cellulose acetate solution was dropped on the spinning membrane (12,000 rpm) and uniformly flowed outwardly by centrifugal force with some degree of penetration into the irregular membrane pores. Two applications of cellulose acetate coating resulted in a homogeneous covering of the porous substrate surface. After complete drying in vacuum, the coated membrane was placed in 0.1N NaOH for 24 hours to hydrolyze and to regenerated the cellulose. The resulting coating thickness was about 1 μm. The molecular cutoff of the coated membrane was about 40,000 daltons.

EXAMPLE 4

The permeability of the regenerated cellulose-Durapore ® composite membrane was compared with an uncoated Durapore ® membrane to glucose and proteins of differing molecular weight. All permeability experiments were carried out in 8 ml stirred diffusion cells at 37° C. The donor cell was filled with the particular macromolecule solution and the receiver cell was filled with plain buffer. The diffusion process was followed by monitoring the increase of permeant concentration in the receiver cell.

The proteins studied (and their method of detection) included: bovine insulin (8 μg/ml-$^{14}$C-insulin, INC, Irvine Calif.), bovine serum albumin "BSA" (1 mg/ml-protein assay at 595 nm, Pierce Chemical Co., Rockford, Ill.), human IgG (1 mg/ml-FITC labelled, Sigma St. Louis, Mo.), aprotinin (100 mg/ml-FITC labelled, Sigma St. Louis, Mo.), and α-lactalbumin (1 mg/ml-FITC labelled, Sigma St. Louis, Mo.).

The $^{14}$C-insulin concentration was determined as a 0.05% solution in scintillation cocktail (BioSafe II, Research Products International, Mt. Prospect, Ill.) and measured on a Beckman 1801 Liquid Scintillation Counter (Beckman Instrument, Inc. Fullerton, Calif.). FTIC labelled proteins were determined with a florometer at an excitation wavelength of 485 nm and an emission wavelength of 515 nm.

The results are given in Table 1 as follows:

TABLE 1

| | Permeability ($cm_2/sec$) | |
|---|---|---|
| Solute (M.W.) | Durapore ® | Cellulose Coated Durapore ® |
| Glucose (180) | $3.93 \times 10^{-7}$ | $1.07 \times 10^{-6}$ |
| Insulin (6,600) | — | $5.17 \times 10^{-8}$ |
| Aprotinin (6,500) | — | $1.22 \times 10^{-8}$ |
| α-Lactalbumin (14,200) | — | $2.53 \times 10^{-9}$ |
| BSA (67,000) | $1.93 \times 10^{-7}$ | NT[1] |
| IgG (Human)(150,000) | $1.13 \times 10^{-7}$ | NT[1] |

[1]NT = Not detectable with Coomassie Protein Assay Reagent (Pierce Chemical Company) which has a sensitivity to 1.0 μg/mL of BSA.

EXAMPLE 5

Pouch Fabrication

An aluminum die for heat sealing was tooled according to the pouch design illustrated in the Figures. Heat sealing of the membranes was obtained by pressing the membrane of Example 3 at 100 psi at 188° C. for at least 6 seconds. The pouch has a side diameter of 4 cm and contained 5 intermittent sealings of 1 mm width which produced a winding pathway between the inlet and outlet providing a reservoir having a volume of about 1 ml. The inlet and outlet portions of the pouch were connected to silastic tubing for external access. A dye solution was used to examine the flow pattern and assure fluid-tight sealing.

EXAMPLE 6

Pouch Filling and Insulin Release

Porcine islets ($2 \times 10^5$) were suspended in 2 ml of RPMI-1640 culture medium supplemented with 10% heat inactivated fetal calf serum, 5.5 mM glucose, 50 mg/ml gentamycin and 2 w/v % of sulfonyl urea grafted poly(NiPAAm). After cooling to 10° C. this suspension, in liquid form, was injected into the pouch prepared according to Example 5 and the inlet and outlet ports were closed.

The filled pouch was immersed in the same culture medium which did not contain the sulfonyl urea grafted poly(NiPAAm) LCST polymer and the temperature was raised to 37° C. in a humidified atmosphere of 5% $CO_2$/95% air.

The insulin release rate from the pouch into the medium was at about 2-3 IU insulin/hr at above 300 mg/dl glucose challenge and about 0.5 IU/hr basal release (50 mg/dl glucose concentration.)

While the above shows a complete and preferred embodiment of the invention they are deemed to be illustrative only as the invention is to be limited only in scope by the claims and functional equivalents thereof.

We claim:

1. A refillable biohybrid artificial pancreas comprising an extravascularly implantable semi-permeable biocompatible membrane pouch having port means connected to subcutaneous access means said pouch having an internal reservoir accessible through said port means said reservoir containing an alternative to encapsulation of each pancreatic islet including a thermosensitive polymeric matrix having entrapped therein pancreatic islets said thermosensitive polymer having an LCST of between about 0° and 40° C. and said semi-permeable membrane having a molecular cutoff of between about 10,000 and 100,000 daltons so as to allow passage of insulin from said pouch and promote metabolic functioning of the islets by allowing, nutrients, ions, oxygen and other materials below the molecular cutoff to enter into the pouch while, at the same time, prohibit bacteria, lymphocytes, and large proteins from entering into the pouch.

2. An artificial pancreas as defined in claim 1 wherein the islets entrapped in said thermosensitive polymeric matrix are generally isolated from each other thereby minimizing aggregation and resistance to mass transport of the insulin when secreted by said islets.

3. An artificial pancreas as defined in claim 2 wherein said pouch reservoir also contains an insulinotropic agent to stimulate insulin secretion from said entrapped islets.

4. An artificial pancreas as defined in claim 3 wherein said insulinotropic agent is a sulfonylurea derivative grafted onto the thermosensitive polymer matrix or onto other water soluble polymers or macromolecules which may be present in said pouch.

5. An artificial pancreas as defined in claim 2 wherein said pouch reservoir also contains one or more polymeric microparticles which release bioactive agents which either promote vascularization at the pouch membrane outer surface or inhibit macrophage activity.

6. An artificial pancreas as defined in claim 5 wherein said polymeric microparticles range in size between about 0.1 to 1000 $\mu$m.

7. An artificial pancreas as defined in claim 6 wherein said microparticles release an agent promoting vascularization at the pouch membrane outer surface.

8. An artificial pancreas as defined in claim 6 wherein said microparticles release an agent inhibiting macrophage activity.

9. An artificial pancreas as defined in claim 2 wherein said thermosensitive polymer is made from the polymerization of at least one monomer selected from the group consisting of N-isopropylacrylamide, N,N-diethylacrylamide, N-acryloylpiperidine, N-methylmethacrylamide, N-ethylmethacrylamide, N-n-propylacrylamide and N-(3'-methoxypropyl)acrylamide.

10. An artificial pancreas as defined in claim 9 wherein said monomer is N-isopropylacrylamide.

11. An artificial pancreas as defined in claim 2 wherein said membrane is a cellulose derivative made from a material selected from the group consisting of cellulose, cellulose hydrate, cellulose acetate, cellulose esters, cellulose ethers, cellulose ester-ethers, cellulose acrylate, cellulose diacrylate, cellulose triacrylate and hydroxypropyl methyl cellulose.

12. An artificial pancreas as defined in claim 2 wherein said membrane is a synthetic polymer made from a material selected from the group consisting of poly(acrylonitrile-co-vinyl chloride), polysulfone, poly(vinylidene fluoride), ethylene vinylacetate, polyethylene, polypropylene, polycarbonate and polytetrafluoroethylene.

13. An artificial pancreas as defined in claim 12 wherein said membrane is a bilaminate comprising said synthetic polymer having a porosity of between about 10 to 95% covered by a thin layer top coating of a cellulose derivative.

14. An artificial pancreas according to claim 2 wherein said port means comprises inlet and exit ports and wherein said subcutaneous access means comprises subcutaneous inlet and exit devices with said inlet and exit ports being connected to said subcutaneous inlet and exit access devices respectively.

15. An artificial pancreas as defined in claim 14 wherein said pouch is relatively flat and comprises opposing generally parallel semi-permeable membrane walls sealed in fluid tight relationship around the perimeter thereof, said opposing membrane walls further being sealed to each other along generally parallel lines intermittently extending from the bottom and top of said pouch structure thereby forming an interior reservoir having a generally winding continuous flowpath and wherein said inlet and exit access ports accessing said reservoir are on opposing ends of said reservoir flowpath.

16. An artificial pancreas as defined in claim 15 wherein said inlet and outlet ports of said pouch interconnect said subcutaneous inlet and outlet access devices by tubing means.

17. An artificial pancreas as defined in claim 15 wherein said pouch membrane has a molecular cutoff of between about 20,000 and 60,000 daltons.

18. An artificial pancreas as defined in claim 15 wherein said relatively flat pouch has a diameter of between about 2 to 15 centimeters.

19. An artificial pancreas as defined in claim 18 wherein said relatively flat pouch has a diameter of between about 4 to 7 centimeters.

20. A method comprising: recharging an artificial pancreas comprising an extravascularly implantable semi-permeable biocompatible membrane pouch having port means connected to subcutaneous access means said pouch having an internal reservoir accessible through said port means said reservoir containing an alternative to encapsulation of each pancreatic islet including a thermosensitive polymeric matrix having entrapped therein pancreatic islets said thermosensitive polymer having an LCST of between about 0° and 40° C. and said semi-permeable membrane having a molecular cutoff of between about 10,000 and 100,000 daltons by the steps of:
(a) lowering the temperature of said resident polymeric matrix in said reservoir to the point that said resident matrix changes phases from a solid to a liquid,
(b) withdrawing from said reservoir, via said port means of said pouch and said subcutaneous access means, said resident polymeric matrix which has been phase changed from solid to liquid,
(c) injecting into said reservoir, via said port means of said pouch and said subcutaneous access means, a fresh liquid phase of thermosensitive polymeric matrix having entrapped therein islets maintained below the LCST of said thermosensitive polymer matrix; and
(d) raising the temperature of the polymeric matrix injected into said reservoir above the LCST causing said polymeric matrix to solidify.

21. A method as defined in claim 20 wherein said pouch contains a single port means and subcutaneous access means for withdrawing and introducing thermosensitive polymer matrix in liquid phase.

22. A method as defined in claim 21 wherein the temperature of said resident polymeric matrix in said reservoir is lowered to the point that said resident matrix changes phases from a solid to a liquid by means of injecting into said reservoir, via said subcutaneous access means and port means of said pouch, a phase change solution having a temperature below the LCST of the resident thermosensitive polymer matrix.

23. A method as defined in claim 22 wherein said phase change solution is an aqueous solution and wherein said phase change solution and resident thermosensitive polymeric matrix in liquid phase are simultaneously withdrawn.

24. A method as defined in claim 23 wherein said aqueous solution is a saline solution.

25. A method as defined in claim 20 wherein said pouch contains a separate port means and subcutaneous access means for introducing and withdrawing thermosensitive polymer matrix in liquid phase such that said port means comprises inlet and exit ports and said subcutaneous access means comprises subcutaneous inlet and exit devices with said inlet and exit ports being connected to said subcutaneous inlet and exit access devices respectively.

26. A method as defined in claim 25 wherein the temperature of said resident polymeric matrix in said reservoir is lowered to the point that said resident matrix changes phases from a solid to a liquid by means a phase change solution having a temperature below the LCST of the resident thermosensitive polymer matrix.

27. A method as defined in claim 26 which comprises the steps:

(a) injecting into said reservoir via said inlet device of said subcutaneous access means and inlet port of said port means of said pouch said phase change solution having a temperature below the LCST of the resident thermosensitive polymer matrix thereby lowering the temperature of said resident polymeric matrix to the point that said resident matrix changes phases from a solid to a liquid, (b) continuously injecting into said reservoir said phase change solution maintained below the LCST of said thermosensitive polymer matrix as in step (a) while simultaneously withdrawing from said reservoir, via said outlet port of said port means and said outlet device of said subcutaneous access means, said resident polymeric matrix which has been phase changed from solid to liquid and continuing said injection of phase change solution and withdrawal of liquid polymer matrix until said resident polymeric matrix has been withdrawn, (c) following the procedure of step (b) continuously injecting into said reservoir a fresh liquid phase of thermosensitive polymeric matrix having entrapped therein islets maintained below the LCST of said thermosensitive polymer matrix while simultaneously withdrawing from said reservoir, said phase change solution and continuing said injection of fresh thermosensitive polymeric matrix and withdrawal of phase change solution until said phase change solution has been withdrawn; and (d) raising the temperature of the polymeric matrix injected into said reservoir above the LCST causing said polymeric matrix to solidify.

28. A method as defined in claims 27 wherein said phase change solution is an aqueous solution.

29. A method as defined in claim 28 wherein said aqueous solution is a saline solution.

* * * * *